(12) United States Patent
Chase

(10) Patent No.: US 12,357,202 B2
(45) Date of Patent: Jul. 15, 2025

(54) DIVERSIFIED GLUCOSE SENSOR SYSTEM

(71) Applicant: Arnold Chase, West Hartford, CT (US)

(72) Inventor: Arnold Chase, West Hartford, CT (US)

(*) Notice: Subject to any disclaimer, the term of this patent is extended or adjusted under 35 U.S.C. 154(b) by 929 days.

(21) Appl. No.: 17/446,572

(22) Filed: Aug. 31, 2021

(65) Prior Publication Data

US 2021/0393174 A1 Dec. 23, 2021

Related U.S. Application Data

(62) Division of application No. 16/118,593, filed on Aug. 31, 2018, now Pat. No. 11,730,403.

(60) Provisional application No. 62/626,788, filed on Feb. 6, 2018.

(51) Int. Cl.
*A61B 5/145* (2006.01)
*A61B 5/00* (2006.01)
*A61B 5/1486* (2006.01)
*A61B 5/15* (2006.01)

(52) U.S. Cl.
CPC ...... *A61B 5/14532* (2013.01); *A61B 5/14865* (2013.01); *A61B 5/150022* (2013.01); *A61B 5/150389* (2013.01); *A61B 5/6849* (2013.01)

(58) Field of Classification Search
CPC ............ A61B 5/14532; A61B 5/14865; A61B 5/150022; A61B 5/150389; A61B 5/6849
See application file for complete search history.

(56) References Cited

U.S. PATENT DOCUMENTS

| | | | |
|---|---|---|---|
| 7,783,333 B2 | 8/2010 | Brister et al. | |
| 2008/0139903 A1 | 6/2008 | Bruce et al. | |
| 2009/0048563 A1 | 2/2009 | Ethelfeld et al. | |
| 2009/0076348 A1* | 3/2009 | Manicka | A61B 5/7282 600/301 |
| 2009/0299301 A1 | 12/2009 | Gottlieb et al. | |
| 2011/0077490 A1 | 3/2011 | Simpson et al. | |
| 2014/0275923 A1* | 9/2014 | Haffner | A61B 5/6867 600/377 |

* cited by examiner

*Primary Examiner* — Jacqueline Cheng
*Assistant Examiner* — Tho Q Tran
(74) *Attorney, Agent, or Firm* — McCormick, Paulding & Huber PLLC

(57) ABSTRACT

A diversified glucose sensor system comprises an introducer needle and two or more independent sensor bodies, each sensor body having one or more sensing elements that can be subcutaneously positioned in a patient's body by insertion of the introducer needle for glucose measurement. The system further includes a progressive insertion device comprising an insertion shaft that pushes the sensor bodies out the end opening of the introducer needle to a desired depth in the patient prior to removal of the insertion shaft and the introducer needle. The sensor bodies are bent or folded and held under stress within the introducer needle for insertion, and released and biased outwardly when pushed out of the introducer needle. The sensing elements are anchored and disposed within the patient at positions providing X/Y/Z-axis diversity for measurement.

11 Claims, 4 Drawing Sheets

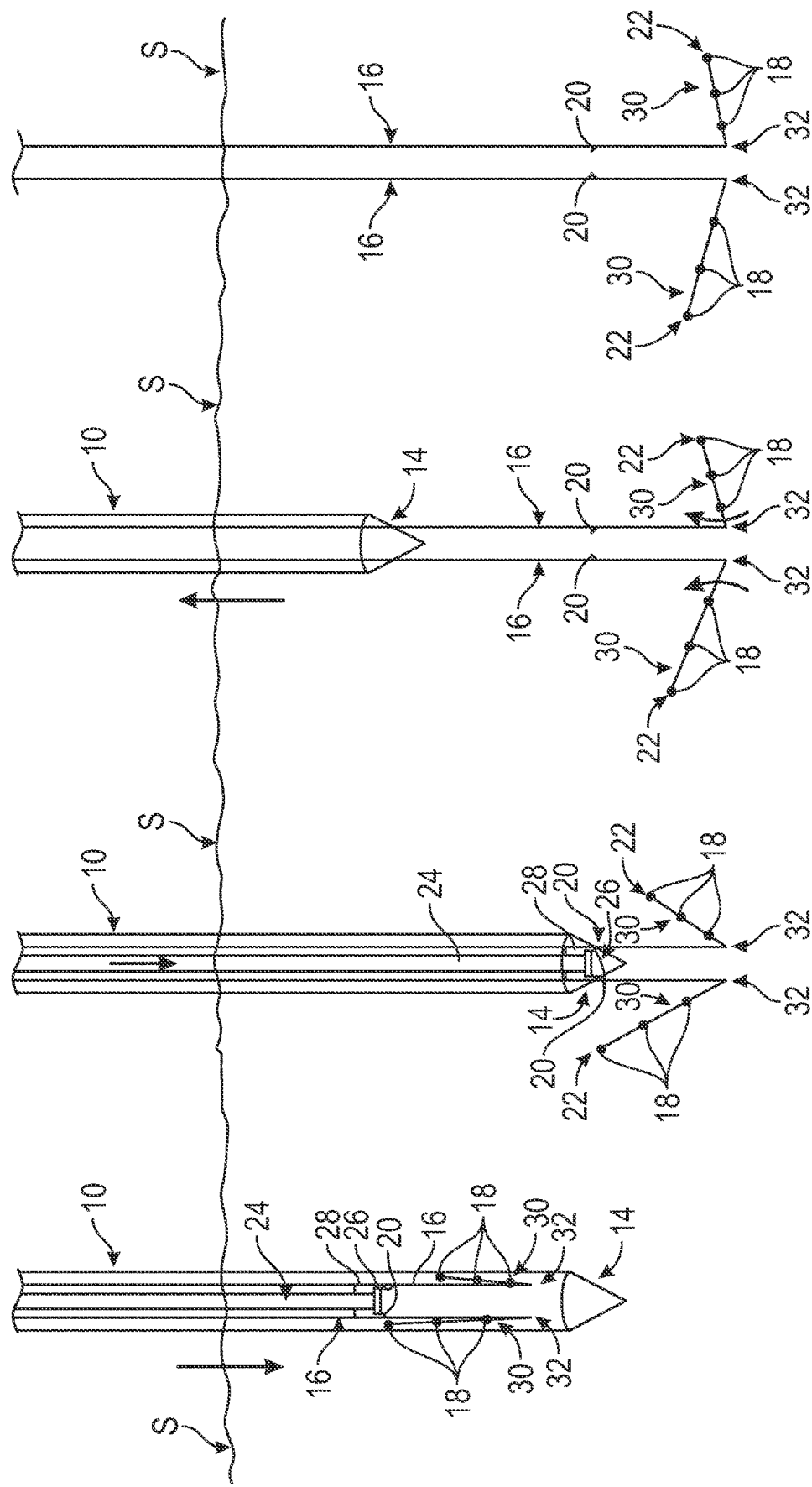

DIVERSIFIED GLUCOSE SENSOR SYSTEM

CROSS-REFERENCE TO RELATED APPLICATIONS

This application is a divisional of U.S. application Ser. No. 16/118,593, filed Aug. 31, 2018, which claims the benefit under 35 U.S.C. § 119(e) of U.S. Provisional Application No. 62/626,788, filed Feb. 6, 2018, each of which is incorporated by reference in its entirety.

TECHNICAL FIELD OF THE INVENTION

The present invention generally relates to blood glucose measurement systems, and more particularly to a subcutaneously disposed blood glucose sensor system with 3-D spatial diversity for optimizing measurements of blood glucose levels in a diabetic patient.

BACKGROUND OF THE INVENTION

Presently there is no practical way of continuously measuring actual blood glucose levels on an in-vivo basis. Technology has evolved to allow blood glucose measurement by measuring the interstitial fluid in a human, which by extrapolation, provides an indirect determination of one's blood glucose levels. The glucose levels in interstitial fluid reflect, on a delayed basis, the blood glucose levels of an individual. However, with current blood glucose sensor designs and technology, measuring errors are problematic and frequent. Unfortunately, for example, sensors for the measurement of interstitial fluid are often subject to physical interference by muscle tissue, bones, contact with veins and arteries, etc., which often create significant reporting errors or sensor failure. Any physical proximity of an interstitial sensing element to a multitude of subcutaneous body parts quickly compromises the ability of the sensing element to deliver an accurate reading, or in extreme cases, provide any meaningful reading at all.

Increasingly, interstitial glucose readings by such sensors are being used to guide or control automatic insulin pumps. Reliance on the use of a single interstitial fluid sensor to make critical real-time treatment decisions creates an extreme risk of the compromise of reliable blood glucose data, and as a result, only systems with multiple sensing elements have been, to-date, approved by the FDA for use with automatic insulin dosing systems.

A typical interstitial fluid sensor utilizes a single subcutaneous point of presence in which to gather glucose readings. As the technology has advanced, however, the use of multiple sampling locations placed linearly on a single sensor body has allowed a very limited, one axis-plane diversity that somewhat reduces the chances for a physical affectation of a single sensing element. For example, prior art designs commonly use three sensing elements spaced along a single sensor body inserted into a patient for measurement. Because the three sensing elements under such prior art designs are used in a generally linear arrangement along a single sensor body, and because data from these closely spaced sensing elements are summed and averaged, there is very limited improvement in the sensing element readings over a single sensing element on a single sensor body, nor improved immunity from physical sensor disruption.

The extremely close spacing of the sensing element locations on a single sensor body for the prior art only truly provides for a "Z" axis (depth) separation. While this is certainly an improvement over the single sensing element approach, and a step in the right direction, this "improved" design still has a high potential to simultaneously compromise all three sensing elements due to the very small actual physical separation of the sensing elements, as well as the fact that all three of the sensing elements reside on the same sensor body which is located within the same general "X/Y" physical location, just at slightly different depths.

In view of the foregoing, there is a need for an improved subcutaneous sensor system for measuring blood glucose levels that features sampling locations that are truly physically diverse in reality, thus resulting in true diversified readings from each sensing element that can be compared with other sensing elements to quickly detect any sensing element error or deviation from the measured data.

While indeed multiple subcutaneous sensors could be individually placed in accordance with prior art methods so as to achieve better physical diversity, this would require multiple subcutaneous insertions using existing methods with a corresponding higher level of insertion trauma.

Accordingly, it is also a general object of the present invention to provide a novel concept, called the Diversified Glucose Sensor System, that provides a new, optimized and efficient approach to blood glucose measurement and monitoring, and moreover, with a single insertion act, improves upon the present small area, linear-only, limited diversity of the prior art designs and technology. Further, it is an object of the present invention to provide a subcutaneous glucose sensor system that improves upon the drawbacks and limitations of prior art systems and methods.

SUMMARY OF THE INVENTION

The novel approach introduced by a diversified glucose sensor system in accordance with the present invention goes beyond the simple linear, small area diversity of the prior art, and introduces automatically propagating, multi-axis physical separation of multiple sensing elements to allow true area diversity from a single insertion process.

Unlike the prior art, the system of the present invention provides an inherent true X/Y/Z physical plane diversity of multiple sensing elements. In accordance with the present invention, the system comprises an introducer needle and two or more independent sensor bodies disposed within the introducer needle for insertion into a patient. Each of said sensor bodies is equipped with one or more sensing elements, and preferably a plurality of spaced sensing elements, that can be subcutaneously positioned in a patient's body by insertion of the introducer needle. The sensor bodies are preferably constructed of a flexible, resilient or "spring like," material and are disposed within the introducer needle under spring bias or stress for insertion into a patient. Alternatively, the sensor bodies may be further designed with integral hinge points that assist in insertion and positioning of the sensor bodies and sensing elements within the patient.

In accordance with presently common uses of subcutaneous sensors, the introducer needle is typically withdrawn after insertion to a desired depth, thereby leaving sensor bodies in place within the patient to a depth of less than the introducer needle. In an embodiment of the present invention, the sensing elements are positioned within a patient using a two-stage progressive insertion device, first comprising introduction of the introducer needle within the patient to an insertion depth, and then a secondary insertion action involving an internal insertion shaft, which pushes the sensor bodies past the end opening of the introducer needle.

In further aspects of the present invention, the sensor bodies are provided with projections, which the insertion shaft contacts to aid in pushing the sensor bodies further past the introducer needle opening.

Unlike the present prior art, which essentially sums the output of three sensing elements "at the source", all of which are inherently subject to common error inducing phenomena, the diversified glucose sensor system of the present invention provides a true and meaningful physical sensing element physical location diversity that provides a much higher degree of accuracy for blood glucose measurement.

Objects, features and advantages of the present invention will become apparent in light of the description of embodiments and features thereof, as enhanced by the accompanying figures.

BRIEF DESCRIPTION OF THE DRAWINGS

FIG. 2 illustrates a cross-sectional view of the assembled insertion device of FIG. 1 after insertion of an introducer needle into the patient.

FIG. 3 illustrates a cross-sectional view of the assembled insertion device of FIG. 1 with an internal insertion shaft used to advance sensor bodies into the patient's body to a position where the folded sensor bodies are pushed past the introducer needle opening.

FIG. 4 illustrates a cross-section view of the insertion device of FIG. 1 with the introducer needle being removed from the patient's body to leave the sensor bodies in place.

FIG. 5 illustrates a side view of the sensor bodies from the insertion device of FIG. 1 as left within the patient's body for use and operation after removal of the introducer needle.

FIG. 6a illustrates the sensor body as folded at a hinge and under a stress, and representative of how the illustrated sensor body is disposed within the introducer needle. FIG. 6b illustrates the sensor body as unfolded about the hinge and free from any stress, and representative of how the sensor body is disposed within a patient.

FIG. 7a illustrates the sensor body as bent and under a stress, and representative of how the illustrated sensor body is disposed within the introducer needle. FIG. &b illustrates the sensor body as flexed out free from a stress, and representative of how the sensor body is disposed within a patient.

FIG. 9a illustrates the sensor body as furled and under a stress, and representative of how the illustrated sensor body is disposed within the introducer needle. FIG. 9b illustrates the sensor body as unfurled and free from a stress, and representative of how the sensor body is disposed within a patient. FIG. 9c illustrates an end view of the unfurled sensor body.

DETAILED DESCRIPTION OF EMBODIMENTS OF THE INVENTION

Figure 1:
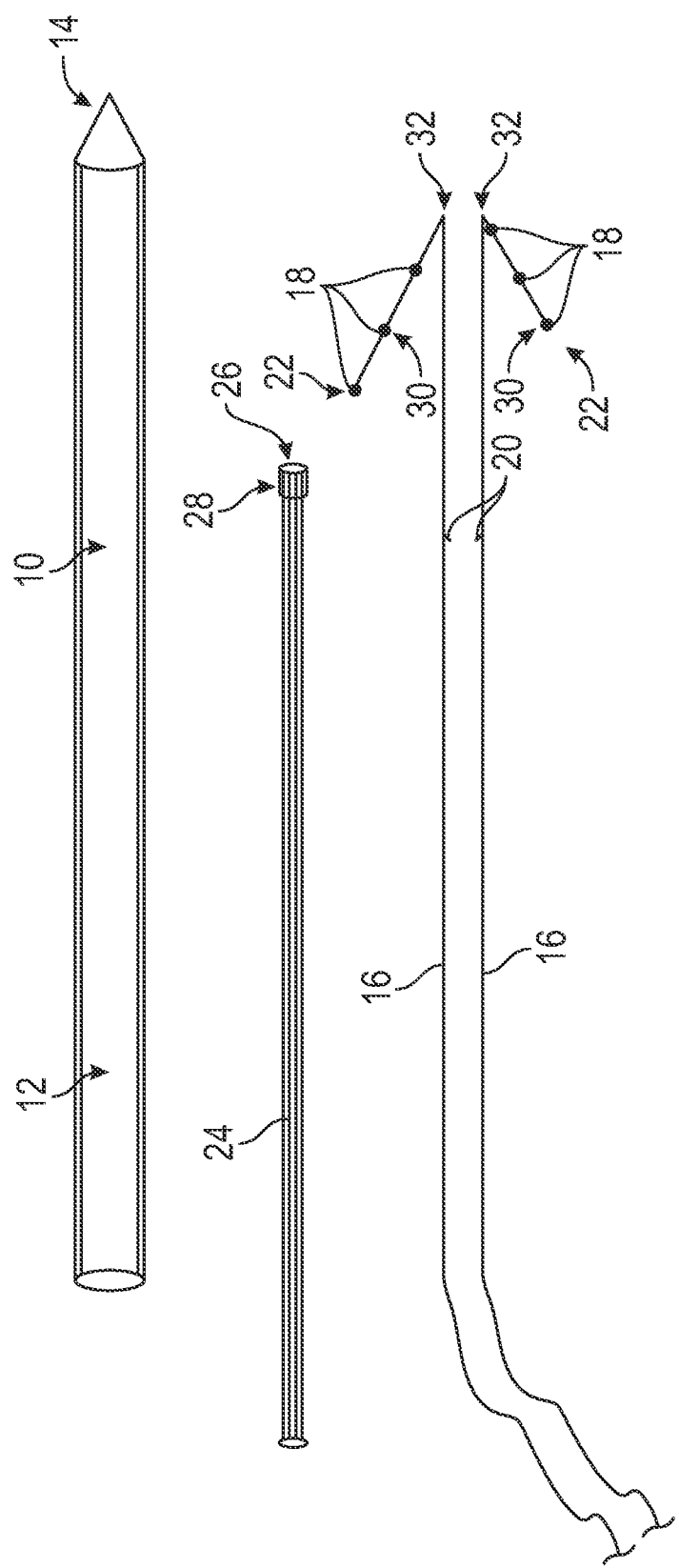
FIG. 1 illustrates the unassembled components of a two-stage progressive insertion device used to subcutaneously insert bent blood glucose sensor bodies in accordance with the present invention into a patient for measurement and monitoring of blood glucose levels.

A diversified glucose sensor system and method for insertion into a patient in accordance with the present invention is generally illustrated in FIGS. 1-5. The system generally comprises use of an introducer needle 10 having a hollow shaft 12 and two or more sensor bodies 16 initially disposed within the hollow shaft 12 of the introducer needle 10 for insertion into a patient. Each sensor body 16 is equipped with one or more sensing elements 18. Using the methodology of the present invention, the sensor bodies 16 can be inserted into the patient so that the sensing elements 18 are subcutaneously positioned in the patient for measurement of the patient's glucose levels.

Preferably, multiple sensing elements 18 are provided on each sensor body 16 so as to increase the measurements obtained for the patient. As illustrated, for example in FIG. 5, each sensor body 16 includes three sensing elements 18. In this regard, the sensing elements 18 are linearly arranged and spaced apart from one another along each sensor body 16 such that, once the sensor body 16 is subcutaneously inserted and positioned in the patient, each sensing element 18 will have a generally unique X/Y/Z position, and the system overall provides collective X/Y/Z sensor diversity for glucose measurement, which is further increased by the use of more than one sensor body 16, each having multiple sensing elements 18, but not necessarily with evenly spaced points. In this regard, the sensing elements 18 may share one dimension position (e.g., the same Z-axis depth) but will have different X- and Y-axis locations, providing overall diversity between the two sensing elements.

Figure 6A:
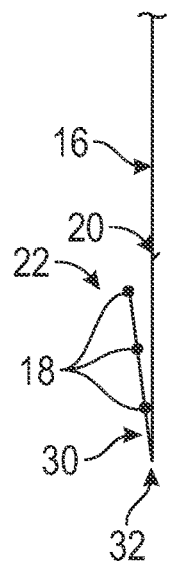
FIGS. 6a and 6b illustrates an embodiment of a sensor body for use with the glucose sensor system of the present invention.
Figure 6B:
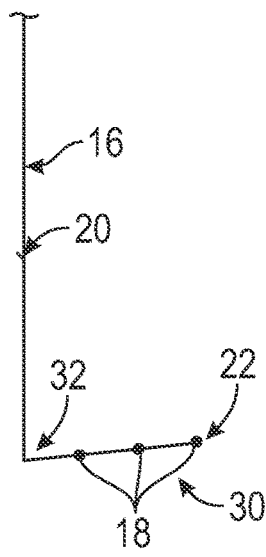
Figure 7A:
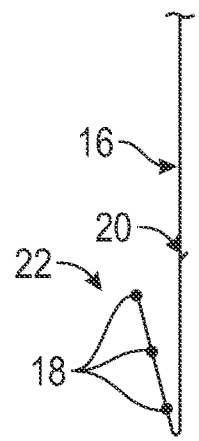
FIGS. 7a and 7b illustrates an alternate embodiment of a sensor body for use with the glucose sensor system of the present invention.
Figure 7B:
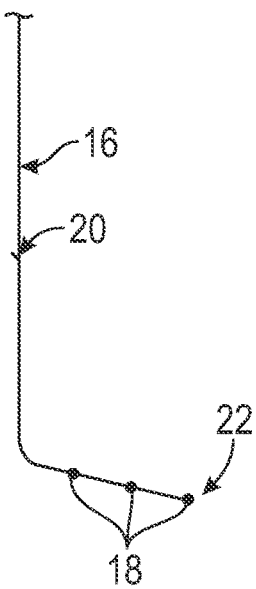
Figures 9A, 9B:
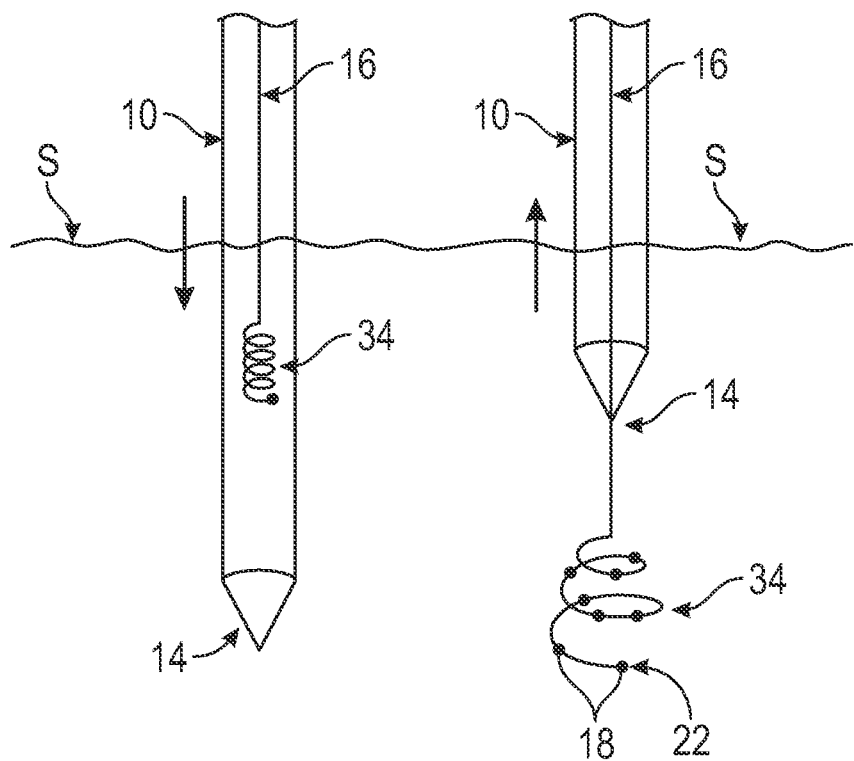
FIGS. 9a, 9b and 9c illustrate another alternate embodiment of a sensor body for use with the glucose sensor system of the present invention.

In accordance with embodiments of the present invention, the sensor bodies 16 are made from a flexible, resilient material and preferably bent under stress within the introducer needle 10 before insertion into the patient. As so bent, the sensor bodies 16 will bias outwardly when released from the introducer needle 10 within the patient's subcutaneous tissue. Additionally, bent sensor bodies 16 will take hold on the patient's tissue once released and when slightly pulled back in accordance with common insertion methods. In accordance with embodiments of the present invention, the sensor body 16 can include a hinge portion 30 that folds up about a hinge 32, preferably under a stress, for storage in the introducer needle 10 and folds out about the hinge 32 for disposal in the patient (FIGS. 6a, 6B), or the sensor body 16 can be simply bent in a spring-biased fashion (FIGS. 7a, 7b), or the sensor body 16 can be helically furled and unfurled (FIGS. 9a, 9b).

Referring to FIG. 2, the system is illustrated at rest—i.e., before full insertion of the sensor bodies 16 into the patient. As illustrated, two sensor bodies 16 reside inside the introducer needle 10 in folded, hinged or otherwise bent condition. In accordance with presently common uses of subcutaneous sensors, the introducer needle 10 is first inserted into the patient by piercing the skin and pushing the needle to a desired insertion depth and fixed subcutaneous inserted position, generally illustrated in FIG. 2. Then, the introducer needle 10 is typically withdrawn, leaving a sensor body 16 in place to a depth of less than the insertion depth of the introducer needle 10 due to the sensor body 16 generally being physically shorter than the introducer needle 10. In accordance with the present invention, a unique and proprietary "two stage" progressive insertion design is used to subcutaneously insert the sensor bodies 16 at a depth below that of the introducer needle 10.

In the present case, after the introducer needle 10 reaches its full insertion depth, a separate secondary insertion action is immediately triggered which pushes the sensor bodies 16 past the end opening 14 of the introducer needle 10. This is accomplished by using an internal insertion shaft 24 having a flattened end 26 that contacts inwardly directed projections, or tiny "barbs", generally designated as reference numeral 20 and provided on each sensor body 16, as illustrated in FIG. 2. That is, as the insertion shaft 24 is advanced within the introducer needle 10, the flattened end 26 contacts the projections 20 and continues to push the sensor bodies 16 forward with movement of the insertion shaft 24. This additional action pushes the front part of the sensor bodies 16 past the introducer needle opening 14 and to a depth deeper within the patient than the insertion depth of the introducer needle 10. This also allows the bent or hinged parts of the sensor bodies 16 that were previously held folded under stress by the introducer needle 10 to effectively release and be freed of the introducer needle's constraint, as generally illustrated in FIG. 2. Although the bent or hinged spring-biased portions of the sensor bodies 16 (now freed of the introducer needle's constraints) start to naturally unfurl by their own "spring-biased" action, this unfurling action is also aided by the withdrawal of the insertion shaft 24 within the introducer needle 10. In this regard, the insertion shaft 24 slightly pulls back on the sensor bodies 16 by friction as the insertion shaft 24 itself is being withdrawn. In the embodiment illustrated in FIG. 3, this friction is increased by providing a foam plug 28 behind the flattened end 26 of the insertion shaft 24. When the insertion shaft 24 is being withdrawn, the foam plug 28 catches and pulls the sensor bodies 16 slightly so that the ends of the sensor bodies 16 can catch onto subcutaneous tissue and anchor in respective desired measurement positions.

In general, the release of the sensor bodies 16 through the end opening 14 of the introducer needle 10 allows an extreme tip 22 of each sensor body 16 to catch on subcutaneous matter or tissue to root the sensor body 16 in place within the patient. However, the very act of withdrawing the insertion shaft 24 further causes the sensor bodies 16 to laterally spread out towards an ideal near-90 degree angle of each sensor body 16, as illustrated in FIGS. 4-5, providing optimal X/Y diversity. The coefficient of friction between the "foam" area 28 and the sensor bodies 16 is chosen to pull the sensor bodies 16 with enough force to assist the unfurling process, while limiting the amount of sensor body travel that would withdraw the sensor bodies 16 excessively.

After the secondary insertion action is complete, the introducer needle 10 is withdrawn in a conventional manner, as illustrated in FIG. 4. Once the introducer needle 10 is withdrawn, the sensor bodies 16 can remain in place for measurements, as illustrated in FIG. 5.

Figure 8A:
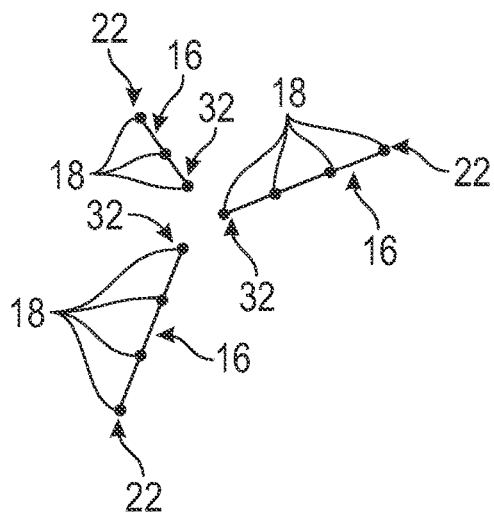
FIGS. 8a and 8b illustrate top views of alternate embodiments of sensor bodies as left within the patient's body for use and operation.
Figure 8B:
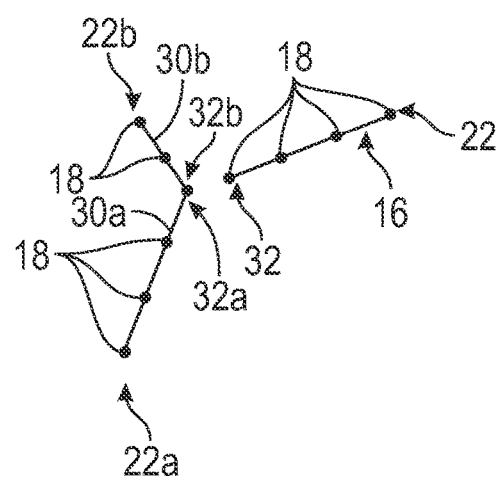

In preferred embodiments of the present invention, at least two sensor bodies 16 are provided for insertion into the patient. In alternate embodiments, three sensor bodies 16 can be used, such as illustrated in FIGS. 8a and 8b. Even more sensor bodies 16 can be provided without departing from the spirit and principles of the present invention.

This entire set-up for a diversified glucose sensor system allows for X/Y/Z axis sensor diversity, while at the same time allowing the sensing elements 18 to be placed at greater subcutaneous depths than the constraints of the introducer needle length would allow in prior art approaches. Because the system allows true X/Y/Z axis sensor diversity, the distances between the sensing elements 18 are far greater than would be possible with a conventional Z-axis only system. This greater physical and spatial separation of the various sensing elements 18 results in a higher chance of accurate sensor readings, with reduced chances of two or more sensing elements 18 being simultaneously compromised by the same body element(s). Additionally, by utilizing X/Y/Z sensor spacing, the system inherently precludes any simultaneous interstitial fluid flow shielding by the same body element(s), which could simultaneously compromise all of the sensing elements 18 in a Z-axis only system. As a further inherent diversity factor, each of the sensor bodies 16 could be manufactured with different "post-hinge" sensor body lengths, as illustrated in FIG. 5, thus adding additional Z-axis depth variation to the X/Y-axes spacing factor, further increasing the total physical and spatial separation of the sensing elements 18, and further improving readings in use. Additionally, the locations of the "barbs" 20 provided on each sensor body 16 may be located at different distances to the hinged area 32, providing additional diversity capability.

Typically, continuous glucose level measurement of interstitial fluid is done in conjunction with the use of an insulin pump. There is, however, known negative interaction between the mechanical infusion of external insulin into a patient's body and the accuracy of a glucose sensor. Current practice calls for an insulin infusion site to be no closer than one inch from a subcutaneously inserted glucose sensing element. As a result of this interaction, under current art, individuals that are using an insulin pump in combination with continuous glucose monitoring must separately insert an insulin-delivering cannula and glucose monitoring sensors at different locations. As a result, individuals utilizing insulin-pump therapy in conjunction with readings from a glucose measurement system must generally make at least two separate physical insertions. With the physical diversity provided by the diversified glucose sensor system of the present invention, an optional variation of the system would allow an insulin infusion cannula and sensor body(s) 16 to be combined into one unit, with its attendant single simultaneous subcutaneous introduction via the progressive insertion method described herein. This variation of the present system, combined with an insulin pump, allows a single infusion and sensing site to safely coexist. Because of the physical diversity provided by the system, a greater than one inch separation is now possible between an insulin cannula that is positioned straight down into the skin, and a sensing element 18 that positions itself greater than one inch away utilizing a folded or hinged sensor body 30, as described herein. Another variation of the "combined" cannula/sensor system could utilize a "folded", spring action cannula, which would add "ultimate" cannula length and thus added infusion site separation distance to the assembly.

An alternate embodiment for the diversified glucose sensor system in accordance with the present invention can combine two "hinged" sensor body segments 30a and 30b on a single shared sensor body 16, such as illustrated in FIG. 8b. One sensor body segment 30a would be a part of the main sensor body 16, attached via a first hinge or bend 32a, while a second hinge or bend 32b and sensor body segment 30b would be attached on a reverse side of the main sensor body 16 from the first "hinge" 32a. Upon insertion into the patient, the two body segments 30a and 30b would release in diverse directions, as illustrated in FIG. 8b.

Figure 9C:
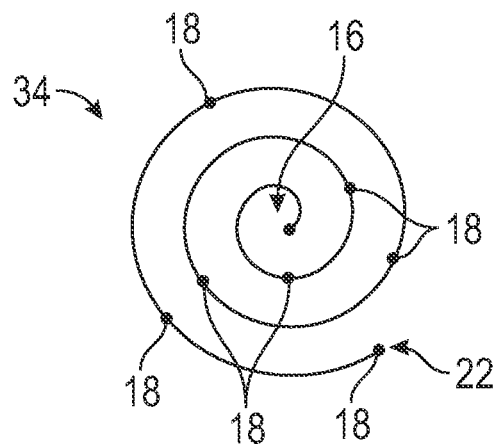

A "spring tension, hinge action" is not the only physical method of achieving a post-introduction diversity movement of the sensor bodies 16. Another alternative embodiment utilizes helically-wound sensor bodies 16 having a helical portion 34, as generally illustrated in FIGS. 9a-9c, which, when disposed within the introducer needle 10 is furled or tightly coiled (FIG. 9a), and when freed of the introducer needle 10, will unfurl in a helical manner (FIGS. 9b, 9c), thus inherently creating movement with physical diversity, either by itself, or in combination with a "hinge action" sensor body within the same introducer needle 10.

It should be noted that depending on how the sensing elements 18 are wired, the diversified glucose sensor system of the present invention can be configured with different sensing element lead combinations. One variation would parallel all sensing element outputs into a single lead set to create a weighted average reading from one set of leads, while another alternate variation would allow each sensing element 18 to provide a discrete reading to a glucose meter via additional operatively connected wire conductors.

The foregoing description of embodiments of the present invention has been presented for the purpose of illustration and description. It is not intended to be exhaustive or to limit the invention to the form disclosed. Obvious modifications and variations are possible in light of the above disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. A method of inserting a sensor into a patient for blood glucose measurement, said method comprising:
   providing an insertion device comprising an introducer needle having a hollow shaft and an opening on a first end thereof;
   providing a sensor system comprising a plurality of sensor bodies each having at least one sensing element configured to detect glucose, and disposing said plurality of sensor bodies within the hollow shaft of the introducer needle;
   inserting the introducer needle into a patient's body until the opening is at a first subcutaneous inserted position;
   withdrawing the introducer needle from the patient's body and leaving the plurality of sensor bodies in place within the patient's body;
   providing an insertion shaft within the introducer needle;
   moving the insertion shaft relative to the introducer needle after the introducer needle has been inserted with its opening at the first subcutaneous inserted position wherein, with such movement, the insertion device pushes the plurality of sensor bodies to a second subcutaneous inserted position within the patient's body beyond the first subcutaneous inserted position; and
   withdrawing the insertion shaft within the introducer needle;
   wherein each sensor body includes a projection which interacts with the insertion shaft to position the sensor bodies within the patient's body at the second subcutaneous inserted position.

2. The method according to claim 1, wherein the insertion shaft includes a flattened portion at a first end thereof, said flattened portion contacting the projection of each sensor body to effect movement thereof.

3. The method according to claim 1, wherein the insertion shaft includes a plug disposed at the first end thereof that frictionally engages each of the plurality of sensor bodies to aide in anchoring of said sensor bodies within the patient when the insertion shaft is being withdrawn.

4. The method according to claim 1, wherein each sensor body is made from a resilient material.

5. The method according to claim 1, wherein at least one of the plurality of sensor bodies has a helical shape.

6. The method according to claim 1, wherein each sensor body has a plurality of sensing elements, said sensing elements being linearly arranged and spaced on the sensor body.

7. The method according to claim 6, wherein the plurality of sensing elements for the plurality of sensor bodies are spaced to have different X, different Y and different Z axis locations from each other when inserted within the patient's body, and wherein the Z axis is in an insertion direction of the introducer needle from an insertion point when inserted within the patient's body.

8. A method of inserting a sensor into a patient for blood glucose measurement, said method comprising:
   providing an insertion device comprising an introducer needle having a hollow shaft and an opening on a first end thereof;
   providing a sensor system comprising a plurality of sensor bodies each having at least one sensing element configured to detect glucose, and disposing said plurality of sensor bodies within the hollow shaft of the introducer needle;
   inserting the introducer needle into a patient's body until the opening is at a first subcutaneous inserted position;
   withdrawing the introducer needle from the patient's body and leaving the plurality of sensor bodies in place within the patient's body;
   providing an insertion shaft within the introducer needle;
   moving the insertion shaft relative to the introducer needle after the introducer needle has been inserted with its opening at the first subcutaneous inserted position wherein, with such movement, the insertion device pushes the plurality of sensor bodies to a second subcutaneous inserted position within the patient's body beyond the first subcutaneous inserted position; and
   withdrawing the insertion shaft within the introducer needle;
   bending each sensor body when it is disposed within the introducer needle such that when the sensor body is pushed past the opening of the introducer needle, the bent portion of the sensor body biases at an end of the sensor body outward;
   wherein the insertion shaft includes a plug disposed at the first end thereof that frictionally engages each of the plurality of sensor bodies to aide in anchoring of said sensor bodies within the patient when the insertion shaft is being withdrawn.

9. A method of inserting a sensor into a patient for blood glucose measurement, said method comprising:
   providing an insertion device comprising an introducer needle having a hollow shaft and an opening on a first end thereof;
   providing a sensor system comprising a plurality of sensor bodies each having at least one sensing element configured to detect glucose, and disposing said plurality of sensor bodies within the hollow shaft of the introducer needle;
   inserting the introducer needle into a patient's body until the opening is at a first subcutaneous inserted position; and
   withdrawing the introducer needle from the patient's body and leaving the plurality of sensor bodies in place within the patient's body;
   wherein each sensor body includes a resilient hinge.

10. The method according to claim 9, further comprising folding each sensor body at the resilient hinge when it is disposed within the introducer needle such that when the sensor body is pushed past the opening of the introducer needle, the folded portion of the sensor body biases outward about the hinge.

11. A method of inserting a sensor into a patient for blood glucose measurement, said method comprising:
- providing an insertion device comprising an introducer needle having a hollow shaft and an opening on a first end thereof;
- providing a sensor system comprising a plurality of sensor bodies each having at least one sensing element configured to detect glucose, and disposing said plurality of sensor bodies within the hollow shaft of the introducer needle;
- inserting the introducer needle into a patient's body until the opening is at a first subcutaneous inserted position;
- withdrawing the introducer needle from the patient's body and leaving the plurality of sensor bodies in place within the patient's body; and
- furling the at least one sensor body when it is disposed within the introducer needle such that when said at least one sensor body is pushed past the opening of the introducer needle, said at least one sensor body unfurls;
- wherein at least one of the plurality of sensor bodies has a helical shape.

* * * * *